United States Patent [19]

Abou-Gharbia

[11] Patent Number: 4,546,186
[45] Date of Patent: Oct. 8, 1985

[54] 1,4,5,6,7,8-HEXAHYDRO-2-METHYL-5-OXO-4-(2-THIAZOLYL)-3-QUINOLINE CARBOXYLIC ACID 2-METHYL(PHENYLMETHYL)AMINO ETHYL ESTER AND PHARMACEUTICALLY ACCEPTABLE SALTS

[75] Inventor: Magid A. Abou-Gharbia, Wilmington, Del.

[73] Assignee: American Home Products Corporation, New York, N.Y.

[21] Appl. No.: 561,423

[22] Filed: Dec. 14, 1983

[51] Int. Cl.[4] .................. C07D 417/04; C07D 401/04; A61K 31/47
[52] U.S. Cl. .................................... 546/167; 544/128; 544/363; 546/104
[58] Field of Search ............... 546/102, 104, 167, 170; 544/128, 363

[56] References Cited

U.S. PATENT DOCUMENTS 4,321,384  3/1982  Sulkowski et al. ................ 546/123
4,380,547  4/1983  Materne ............................ 546/280

FOREIGN PATENT DOCUMENTS 2003148  7/1971  Fed. Rep. of Germany ...... 546/170
1430961  4/1976  United Kingdom .

OTHER PUBLICATIONS

Murakami et al., Chemical Abstracts, vol. 79, 105084q, (1973).

Primary Examiner—Donald G. Daus
Assistant Examiner—Diana G. Rivers
Attorney, Agent, or Firm—Richard K. Jackson

[57] ABSTRACT 1,4,5,6,7,8-Hexahydro-4-heterocyclyl-5-oxo-quinoline derivatives and corresponding acridine derivatives and pharmaceutically acceptable salts thereof are useful antihypertensive agents.

1 Claim, No Drawings

1,4,5,6,7,8-HEXAHYDRO-2-METHYL-5-OXO-4-(2-THIAZOLYL)-3-QUINOLINE CARBOXYLIC ACID 2-METHYL(PHENYLMETHYL)AMINO ETHYL ESTER AND PHARMACEUTICALLY ACCEPTABLE SALTS

BACKGROUND OF THE INVENTION

Pharmacological agents possessing the ability to block cellular transmembrane influx of calcium are capable of suppressing that portion of myocardial or smooth muscle contractility which is dependent upon extracellular calcium. These pharmacological agents, termed calcium antagonists, have been proven to be useful in the treatment of hypertension, cardiac arrhythmias, angina pectoris, cardiac myopathy and coronary artery vasospasm (a possible cause of sudden cardiac death syndrome). Can. J. Physiol. Pharmacol., 57, 433 (1979); Drugs, 15, 169 (1978); Acta Pharmacol. Toxicol., 43, suppl. 1,45 (1978).

In theory, calcium antagonists are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. Acta Pharmacol. Toxicol., 43, 5 (1978); loc cit. 291 (1978); Microvascular Res., 5, 73 (1973); Am. Rev. Pharmacol. Toxicol., 17, 149 (1977). Calcium channels of tissues which are most sensitive to calcium antagonist blockade are those which allow calcium influx only when the cell membranes are electrically depolarized. Alpha-adrenergic receptor-activated calcium channels are relatively unaffected by these agents. Circ. Res., 46, 246 (1980). This observation provides basis for evaluation of calcium antagonism.

The vascular smooth muscle tissue from the rabbit aorta can be made to contract when exposed to a depolarizing solution containing an elevated potassium ion concentration and normal amounts of calcium ions. Calcium antagonists added to the solution produce a dose dependent relaxation of the contracted rabbit aortic tissue. Normal contraction of the aortic tissue can then be induced in the presence of a calcium antagonist by subsequent addition of an alpha-adrenergic agonist, such as norepinephrine, to the solution. Eur. J. Pharmacol., 53, 281 (1979); Circ. Res., 46, 426 (1980); J. Exp. Pharmacol. Therap., 174, 500 (1970). The normal contraction produced by an alpha-adrenergic agonist after maximal smooth muscle relaxation has been induced by a calcium antagonist, serves to distinguish the calcium blocking effect of an agent from a nonspecific depressant effect on the muscle.

DESCRIPTION OF THE INVENTION

In accordance with this invention there is provided a group of 1,4,5,6,7,8-hexahydro-4-heterocyclyl-5-oxo-quinoline derivatives and corresponding acridine derivatives and pharmaceutically acceptable salts thereof which compounds are calcium antagonists useful in the treatment of hypertension, cardiac arrhythmias, angina pectoris, cardiac myopathy and coronary artery vasospasm.

More specifically, the antihypertensive agents of this invention are compounds of the formula:

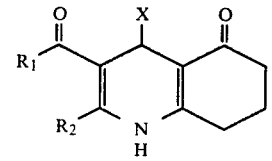

in which
$R_1$ is alkoxy of 1 to 6 carbon atoms, alkoxyalkoxy of 2 to 12 carbon atoms, or $OCH_2(CH_2)_n\text{-}NR_3R_4$ wherein $R_3$ is hydrogen or alkyl of 1 to 6 carbon atoms, $R_4$ is alkyl of 1 to 6 carbon atoms or aralkyl of 7 to 10 carbon atoms and $R_3$ and $R_4$ taken together with the nitrogen atom to which they are attached form an imidazolidinyl, pyrrolidinyl, piperidinyl, piperazinyl, 4-alkylpiperazinyl in which the alkyl group contains from 1 to 6 carbon atoms or morpholinyl, and n is one of the integers 0, 1 or 2;

$R_2$ is alkyl of 1 to 6 carbon atoms or trifluoromethyl;
$R_1$ and $R_2$ taken together represent trimethylene; and
X is substituted or unsubstituted imidazolyl or thiazolyl, wherein said substituent is alkyl of 1 to 6 carbon atoms or aryl of 6 to 10 carbon atoms;
or a pharmaceutically acceptable salt thereof.

The preferred compound subgenus from the standpoint of economics and ease of obtaining the reactants embraces compounds of the formula:

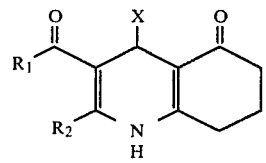

in which
$R_1$ is alkoxy of 1 to 3 carbon atoms, or $-OCH_2(CH_2)_n-NR_3R_4$ where $R_3$ is hydrogen or alkyl of 1 to 3 carbon atoms, $R_4$ is alkyl of 1 to 3 carbon atoms or benzyl and $R_3$ and $R_4$ taken together with the nitrogen atom to which they are attached form 2-imidazolidinyl, 2-pyrrolidinyl, 2-piperidyl, 1-piperazinyl, 4-alkylpiperazin-1-yl in which the alkyl group contains 1 to 3 carbon atoms or 3-morpholinyl and n is one of the integers 1 or 2;

$R_2$ is alkyl of 1 to 3 carbon atoms or trifluoromethyl, and $R_1$ and $R_2$ taken together represent trimethylene;
X is substituted or unsubstituted imidazol-2-yl or thiazol-2-yl, wherein said substituent is alkyl of 1 to 3 carbon atoms or aryl of 6 to 8 carbon atoms;
or a pharmaceutically acceptable salt thereof.

The quinoline derivatives of this invention are prepared by reaction of equimolar amounts of 1,3-cyclohexanedione, a heterocyclic aldehyde and a 3-alkyl-3-amino-acrylic acid ester as follows:

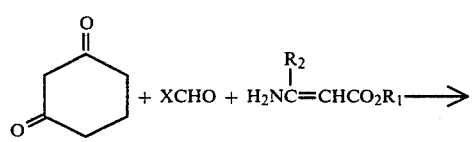

-continued

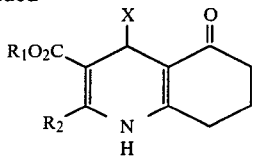

Similarly, the acridine derivatives of this invention are prepared by reaction of two equivalents of 1,3-cyclohexanedione, one equivalent of the heterocyclic aldehyde and ammonium acetate, thusly:

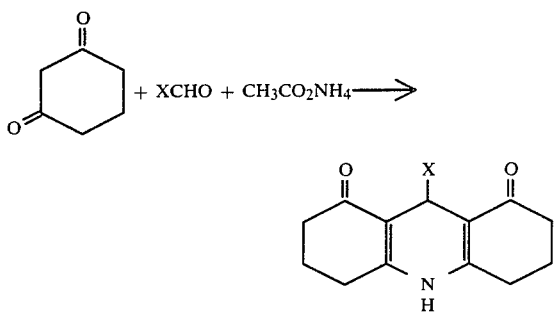

The heterocyclic aldehydes employed in the production of the compounds of this invention are either known compounds or may be prepared by standard procedures (Tetrahedron, 1980, 36, 2505 or Org. Prep and Proced., 1983, 15 19). The aminoalkyl esters may be prepared by formation of the substituted aminocrotonate in situ via ammonolysis of the desired aminoalkyl acetoacetic acid ester.

The pharmaceutically acceptable salts of the antihypertensive agents of this invention are prepared directly by neutralization of the free base or by metathetical displacement. The physiological acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicyclic, lactic, naphthalenesulfonic acid, and the like.

The compounds of this invention were initially shown to exhibit $Ca^{+2}$ antagonism in rabbit aortic strips wherein the strips were contracted in an organ bath containing a modified physiological salt solution (Broekaert et al., Europ. J. Pharmacol. 53 281 (1979)) in which 100 millimoles potassium ion had been substituted on an equimolar basis for sodium ion. After a stable active tension has developed in the strip, as measured by Statham UC-2 force transducers and recorded on an eight channel Beckman Dynograph Polygraphic Recorder, an amount of the antagonist was added to the organ bath to make a $10^{-5}$ molar concentration of antagonist. The depressent effect, expressed as percent relaxation, was taken from the mean of at least two experiments. After maximum $Ca^{+2}$ antagonist induced relaxation was obtained, a maximal dose of norepinephrine ($10^{-5}$ moles) was added to the organ bath to determine whether normal alpha-adrenergic responses were still effected and show that the compound being tested was not a general depressant.

The in vivo blood pressure lowering ability of the compounds of this invention was established by measuring the systolic pressure of spontaneously hypertensive rats with a Decker Caudal Plethysmograph or similar sensor device. The compound being tested is administered to groups of four rats and their blood pressure is read prior to compound administration and at 1.5 and 4 hours after compound administration. Depending upon the behavior of the compound being tested, the schedule of blood pressure readings and route of administration is modifed. Initially the compounds are administrered orally but where compound solubility is a factor, the compounds may be administered parenterally (i.e., i.p., i.m., s.c., i.v., etc.) as desired. The compounds of this invention were initially administered orally at a standard testing dose of 50 mg/kg.

Based upon the activity profile elicited by the compounds of this invention in the above-described standard scientifically recognized test models, the compounds are established as hypotensive agents useful in the treatment of hypertension and conditions characterized by constrictive blood flow in coronary arteries. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 10 to about 50 milligrams per kilogram host body weight to be administered in single or plural doses as needed to obtain the desired hypotensive response. The specific dosage regimen for a given patient will depend upon age, pathological state, severity of dysfunction, size of the patient, etc. Oral administration is performed with either a liquid or solid dosage unit in any conventional form such as tablets, capsules solutions, etc., which comprise a unit dose (e.g. from about 25 milligrams to about 4 grams) of the active ingredient alone or in combination with adjuvants needed for conventional coating, tableting, solubilizing, flavor or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the antihypertensive activity is reported as a decrease in blood pressure (B.P.) in terms of millimeters of mercury (mmHg) at the time indicated after 50 mg/kg oral dosing. Similarly, the $Ca^{+2}$ antagonist activity of the compound is presented in terms of present relaxation (P.R.) at $10^{-5}M$ concentrations.

EXAMPLE 1

1,4,5,6,7,8-Hexahydro-2-methyl-4-(1-methyl-1H-imidazol-2-yl)-5-oxo-3-quinolinecarboxylic acid ethyl ester A mixture of N-methyl-imidazole-2-carboxaldehyde (4.9 g, 0.045 mole), 1,3-cyclohexandione (5.8 g, 0.045 mole), and ethyl-3-aminocrotonate (5.04 g, 0.045 mole), in 50 mL of absolute ethanol was refluxed for 24 hours. The reaction mixture was cooled and the separated solid was filtered and recrystallized from a hexane-ethylacetate (1:1) mixture to afford 5.2 g (37% yield) of the title compound, m.p. 271°–272° C.; MS, m/e 315 (M+); NMR (CDCl$_3$) δ 1.0 (t, 3 H, CCH $_3$), 1.5–2.4 (m, 6 H, cyclohexanone), 2.5 (s, 3 H, =CCH$_3$), 3.9–4.1 (q, 2 H, CH$_2$C), 4.0 (s, 3 H, NCH$_3$), 5.2 (s, 1 H, dihydropyridine-H), 6.3 (d, 1 H, imidazole-H), 6.5 (d, 1 H, imidazole-H) and 9.5 (s, 1 H, NH).

Analysis for: $C_{17}H_{21}N_3O_3$

Calculated: C, 64.76; H, 6.66; N, 13.33.
Found: C, 64.28; H, 6.72; N, 13.00.
B.P. = −22 at 1.5 hours and −18 at 4 hours.
P.R. = 14.

EXAMPLE 2

1,4,5,6,7,8-Hexahydro-2-methyl-5-oxo-4-(2-thiazolyl)-3-quinoline carboxylic acid 2-Methyl(phenylmethyl)amino ethyl ester To a mixture of 1,3-cyclohexandione (5.6 g, 0.05 mole), 2-(N-benzyl-N-methylamino)ethyl acetoacetate (12.4 g, 0.05 mole) and ammonium acetate (7.7 g, 0.1 mole) in 50 mL of absolute ethanol was added (5.5 g, 0.05 mole) of thiazole-2-carboxaldehyde and the reaction mixture was heated at reflux for 12 hours. The solution was cooled, evaporated under reduced pressure, and the residue was extracted in 200 ml of methylene chloride. The methylene chloride layer was washed with water, dried and evaporated in vacuo. The brown oil was separated by high performance liquid chromatography (using 30% methanol-ethyl acetate mixture as the eluent) to afford 9.0 g (43% yield) of the title compound, m.p. 119°–120° C.; MS, m/e 437 (M+); NMR (CDCl$_3$) δ 1.6–2.5 (m, 6 H, cyclohexanone), 2.2 (s, 3H, CCH$_3$), 2.3 (s, 3 H, NCH$_3$), 3.5 (s, 2 H, CH$_2$φ), 3.6 (t, 2 H, CCH$_2$N), 4.1 (t, 2 H, OCH$_2$C), 5.5 (s, 1 H, dihydropyridine-H), 7.1 (d, 1H, thiazole-H), 7.2 (s, 5H, φ), 7.6 (d, 1 H, thiazole-H) and 8.6 (s, 1 H, NH).

Analysis for: $C_{24}H_{27}N_3SO_3$
Calculated: C, 65.90; H, 6.17; N, 9.61.
Found: C, 65.83; H, 6.22; H, 9.51.

The dihydrochloride salt was prepared by dissolving the title compound in ethanol saturated with hydrogen chloride gas. The alcohol was evaporated, and the residue was recrystallized from ethanol, m.p. 154°–158° C.
B.P. = −47 at 1.5 hours.
P.R. = 21.1.

EXAMPLE 3

1,4,5,6,7,8-Hexahydro-2-trifluoromethyl-4-(1-methyl-1H-imidazol-2-yl)-5-oxo-3-quinolinecarboxylic acid ethyl ester To a stirred mixture of 2.3 g (0.02 mole) of 1,3-cyclohexandione, ethyl-4,4,4-trifluoroacetoacetate (3.3 g, 0.02 mole) and ammonium acetate (4.9 g, 0.4 mole) in 50 mL of absolute ethanol, (2.0 g, 0.02 mole) of N-methylimidazole-2-carboxaldehyde was added. The reaction mixture was refluxed for 24 hours and allowed to cool to room temperature. The solvent was evaporated in vacuo, and the residue was separated by high performance liquid chromatography (30% methanol-ethylacetate mixture as the eluent) to afford 0.5 g (7% yield ) of the title compound, m.p. 197°–198° C.; MS, m/e 369 (M+); NMR (CDCl$_3$) δ1.0 (t, 3 H, CCH$_3$), 1.5–2.4 (m, 6 H, cyclohexenone), 3.7 (s, 3 H, NCH$_3$), 4–4.1 (q, 2 H, CH$_2$C), 5.0 (s, 1 H, dihydropyridine-H), 6.5 (d, 1 H, imidazole-H), 6.8 (d, 1 H, imidazole-H) and 9.6 (s, 1 H, NH).

Analysis for: $C_{17}H_{18}F_3N_3O_3 \cdot \frac{1}{2}H_2O$
Calculated: C, 53.96; H, 5.02; N, 11.11.
Found: C, 54.30; H, 5.01; N, 10.80.
B.P. = −10 at 4 hours (at a dose of 35 mg/kg).
R.P. = 10.8.

EXAMPLE 4

1,4,5,6,7,8-Hexahydro-4-(thiazol-2-yl)-5-oxo-3-quinolinecarboxylic acid ethyl ester The procedure of Example 1 was utilized with the exception that thiazole-2-carboxaldehyde was used instead of N-methyl-imidazole-2-carboxaldehyde to afford 72% yield of the title compound, m.p. 239°–240° C., MS, m/e 318 (M+); NMR (CDCl$_3$) δ 1.1 (t, 3 H, CCH$_3$), 1.9–2.5 (m, 6 H cyclohexanone), 4.0 (q, 2 H, CH$_2$C), 5.4 (s, 1 H, dihydropyridine-H), 7.5 (d, 1 H, thiazole-H), 7.7 (d, 1 H, thiazole-H), and 8.0 (s, 1 H, NH).

Analysis for: $C_{16}H_{18}N_2SO_3$
Calculated: C, 60.37; H, 5.66; N, 8.80.
Found: C, 60.28; H, 5.84; N, 8.68.
B.P = −21 at 4 hours.
P.R. = 9.

EXAMPLE 5

1,4,5,6,7,8-Hexahydro-2-methyl-5-oxo-4-(1-methyl-1H-imidazol-2-yl)-3-quinolinecarboxylic acid 2-methyl(phenylmethyl)amino ethyl ester The procedure in Example 2 was utilized with the exception that N-methylimidazole-2-carboxaldehyde was used instead of thiazole-2-carboxaldehyde to afford 4.9 g (22% yield) of the title compound, m.p. 184°–187° C.; MS, m/e 434 (M+).

Analysis for: $C_{25}H_{30}N_4O_3 \cdot H_2O$
Calculated: C, 66.37; H, 7.0; N, 12.3.
Found: C, 66.83; H, 6.81; N, 12.74.
B.P. = −13 at 4 hours.
P.R. = 11.3

EXAMPLE 6

3,4,6,7,9,10-Hexahydro-9-(2-thiazolyl)-1,8(2H,5H)-acridine

A mixture of 5.08 (0.045 mole) of thiazole-2-carboxaldehyde, 11.6 g (0.09 mole) of 1,3-cyclohexanidione and (5.0 g, 0.06 mole) of ammonium acetate in 50 mL of absolute ethanol were refluxed for 24 hours. The reaction mixture was cooled and filtered. The solid was recrystallized from ethanol to afford 3.7 g (30% yield) of the title compound, m.p. 278°–281° C.; MS, m/e 300 (M+); NMR (CDCl$_3$) δ1.7–2.1 (m, 6 H, cyclohexenone), 2.5–2.6 (m, 6 H, cyclohexenone), 5.4 (s, 1 H, dihydropyridine-H), 7.8 (d, 1 H, thiazole-H), 7.9 (d, 1 H, thiazole-H) and 9.7 (s, 1 H, NH).

Analysis for: $C_{16}H_{16}N_2SO_2$
Calculated: C, 64.00; H, 5.3; N, 9.33; S, 10.66.
Found: C, 63.68; H, 5.33; N, 9.13; S, 10.42.

The hydrochloride salt was prepared following the procedure described in Example 2, m.p. 234°–235° C.
Analysis for: $C_{16}H_{16}N_2SO_2 \cdot HCl$
Calculated: C, 57.05; H, 5.05; N, 8.32.
Found: C, 56.79; H, 5.0; N, 8.16.
B.P. = −19 at 4 hours.

EXAMPLE 7

3,4,6,7,9,10-Hexahydro-9-(1-methyl-1H-imidazol-2-yl)-1,8(2H,5H)-acridine

The procedure in Example 6 was utilized with the exception that N-methylimidazole-2-carboxaldehyde was used instead of thiazole-2-carboxaldehyde to afford 9.2 g (69% yield) of the title compound, m.p. 285°–287° C.

Analysis for: $C_{17}H_{19}N_3O_2$
Calculated: C, 68.68; H, 6.39; N, 14.14.
Found: C, 68.82; H, 6.52; N; 13.93.
B.P. = −4 at 1.5 hours.

What is claimed is:

1. The compound which is 1,4,5,6,7,8-hexahydro-2-methyl-5-oxo-4-(2-thiazolyl)-3-quinoline carboxylic acid 2-methyl(phenylmethyl)amino ethyl ester or a pharmaceutically acceptable salt thereof.

* * * * *